United States Patent [19]

Beeler

[11] Patent Number: 5,068,947
[45] Date of Patent: Dec. 3, 1991

[54] SEPARATION APPARATUS

[75] Inventor: Alfred Beeler, Horgen, Switzerland

[73] Assignee: Siegfried Peyer AG, Wollerau, Switzerland

[21] Appl. No.: 568,044

[22] Filed: Aug. 16, 1990

[30] Foreign Application Priority Data

Aug. 29, 1989 [CH] Switzerland ............................ 135/89

[51] Int. Cl.⁵ ...................... D01G 15/50; D01G 19/00
[52] U.S. Cl. .................... 19/106 A; 19/58; 19/233; 19/297
[58] Field of Search ......................... 19/59, 60, 96, 100, 19/106 R, 106 A, 112, 115 R, 150, 101.1, 297, 306, 48 A, 58, 223

[56] References Cited

U.S. PATENT DOCUMENTS

| 4,901 | 12/1846 | Keith | 19/58 |
|---|---|---|---|
| 547,336 | 10/1895 | Crowder | 19/58 |
| 723,035 | 3/1903 | Ruth | 19/58 |
| 1,018,273 | 2/1912 | Rozier | 19/58 |
| 1,554,530 | 9/1925 | Sheehan | 19/106 A |
| 2,413,832 | 1/1947 | Kay et al. | 19/106 R |
| 2,867,850 | 1/1959 | Mayer et al. | 19/58 |
| 2,977,641 | 4/1961 | Brooks | 19/58 X |
| 3,345,698 | 10/1967 | Anton | 19/106 A |
| 3,355,774 | 12/1967 | Miyagi | 19/106 A |
| 3,362,048 | 1/1968 | Hale et al. | 19/106 A |
| 3,370,326 | 2/1968 | Law | 19/106 |
| 3,793,680 | 2/1974 | Ota | 19/106 R |

FOREIGN PATENT DOCUMENTS

| 0470213 | 12/1928 | Fed. Rep. of Germany | ... 19/106 A |
|---|---|---|---|
| 1341775 | 11/1963 | France . | |
| 0002637 | 9/1862 | United Kingdom | ............. 19/106 A |
| 0002694 | 10/1862 | United Kingdom | ............. 19/106 A |
| 0008396 | 5/1884 | United Kingdom | ............. 19/106 A |
| 0023342 | of 1902 | United Kingdom | ............. 19/106 A |
| 1162380 | 8/1969 | United Kingdom | ............. 19/106 A |

OTHER PUBLICATIONS

Band 27, Juni 1968, "Technisch nieuws", Bladzijde 353-354 siehe Kapitel. Spinnerij, Abschnitt, Apparaat voor het trekken van Kambandmonsters.

Primary Examiner—Werner H. Schroeder
Assistant Examiner—Ismael Izaguirre
Attorney, Agent, or Firm—Walter C. Farley

[57] ABSTRACT

A separation apparatus for fiber webs (6) with parallelized fiber positions wound on a processing drum (4) includes an arm (1) rocking relative to the processing drum, the arm carrying a separation comb (13). The arm and its separation comb (13) are mounted for movement along and controlled by the shape of a separation cam (3) implementing the separation of the fiber web (6) wound on the processing drum (4) at a specified site and the unwinding of the separated fiber web from the processing drum (4) by the free end of the fiber web (6) along a generatrix of the surface of the processing drum (4).

10 Claims, 3 Drawing Sheets

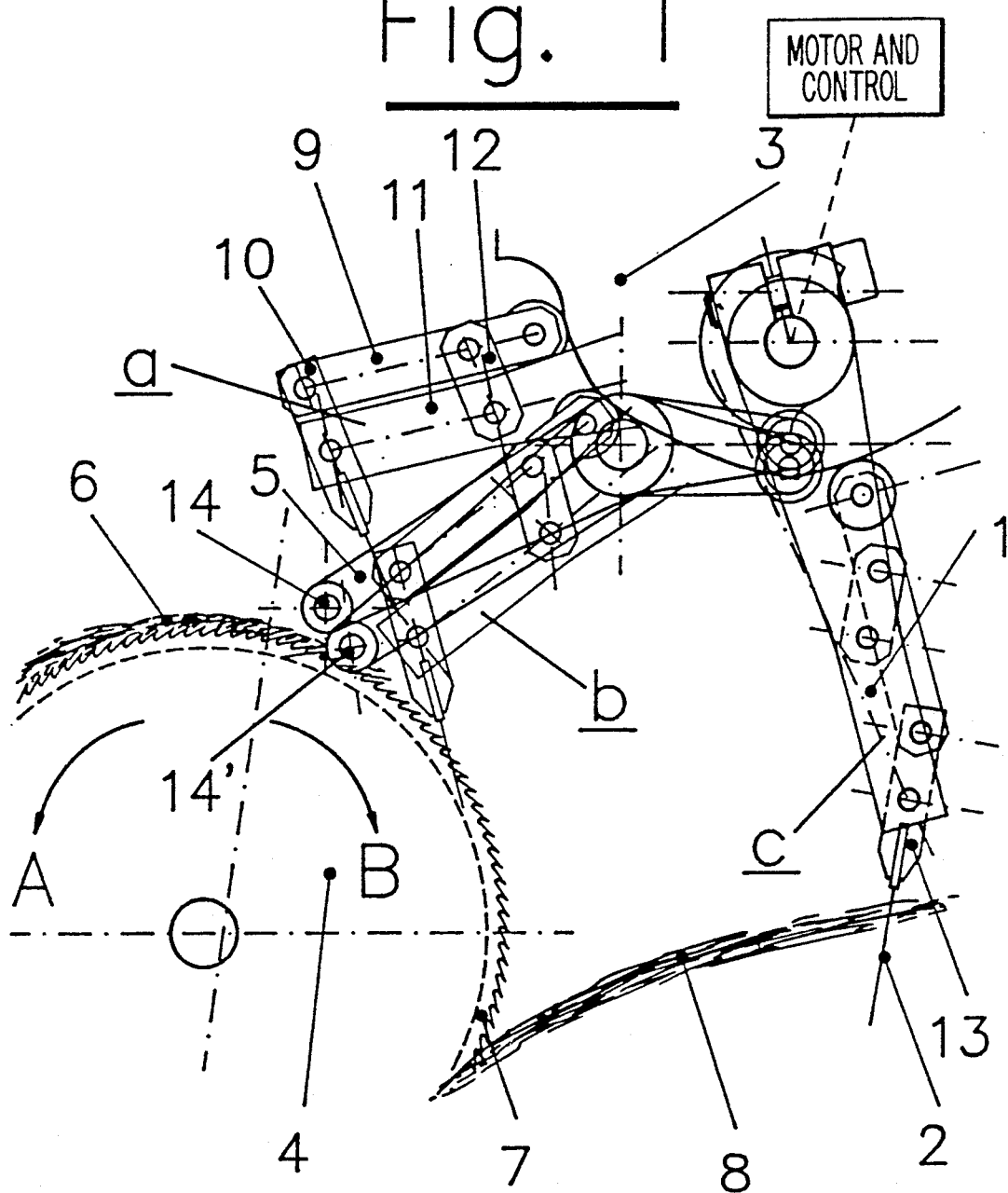
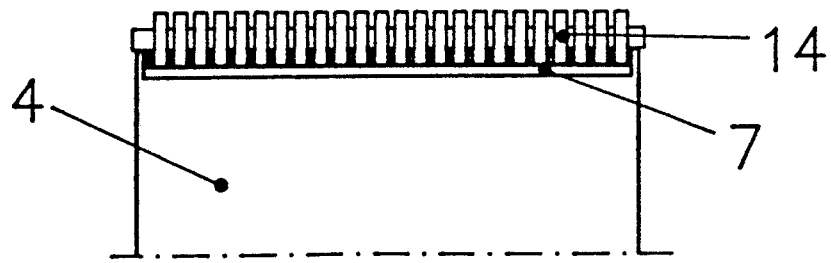

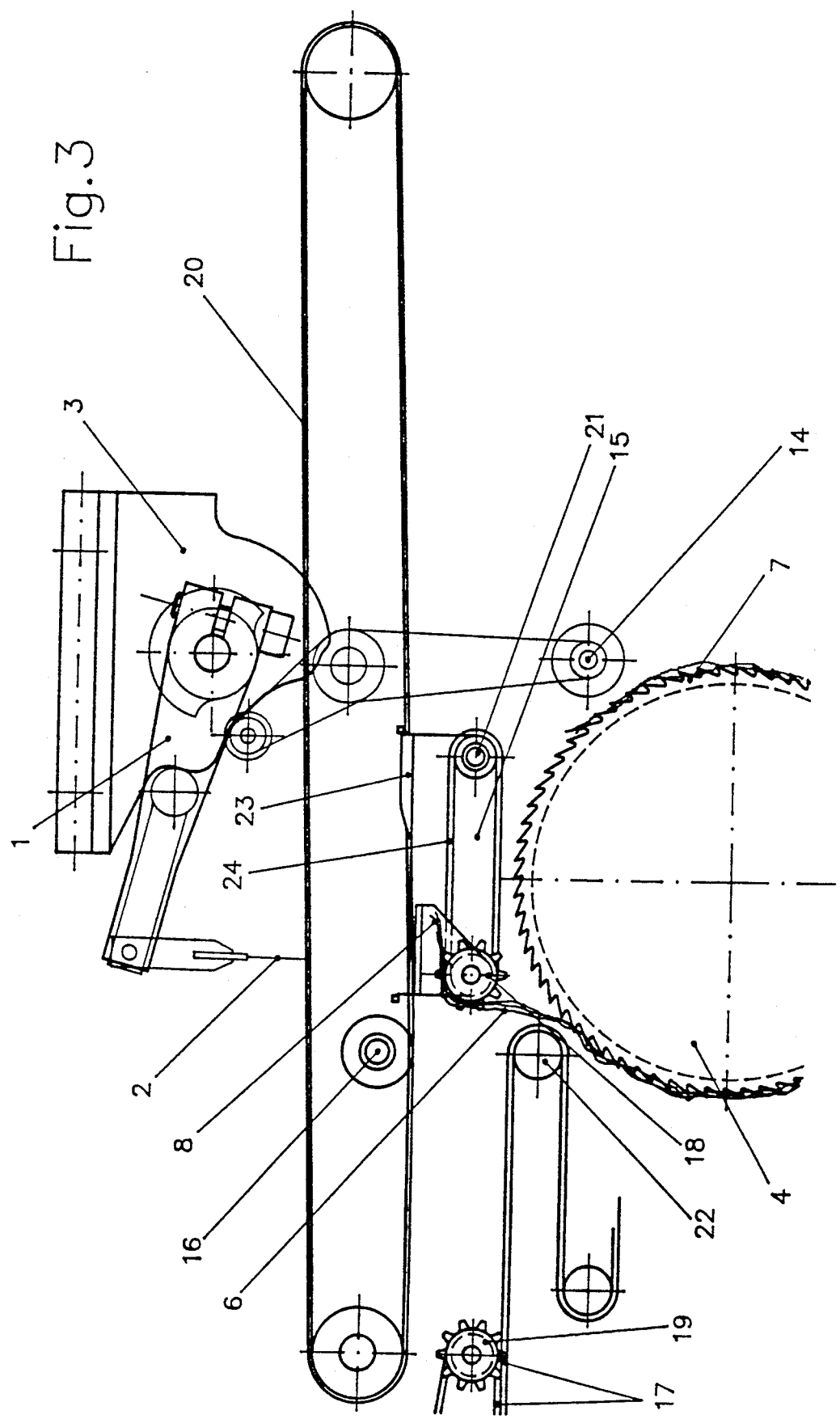

SEPARATION APPARATUS

FIELD OF THE INVENTION

This invention relates to a separation system for separating textile fibers from a drum for testing.

BACKGROUND OF THE INVENTION

Many procedures and apparatus are available for testing textile fibers qualitatively and quantitatively. With many testing methods, the disordered fiber material—for instance floccular cotton—cannot be measured directly but instead must first be prepared into fiber strips with parallelized fiber positions. Such preparallelized fiber strips accordingly are the input to all test equipment which for testing require pre-parallelized fibers.

Such equipment for instance includes:
fiber aligners to array the ends of fiber tufts
brushing stations for fiber tufts without end arrays
tensile apparatus to determine the elongation and tear-resistance of bundles
optical scanners such as image-data analyzers
fiber-tear testers
fiber fineness testers
fiber sorting devices etc.

There is need in equipment of these types to detach the fiber strip several times from a processing drum in order to subject it to a further processing cycle. As to manually operated devices (see special print of G. Spiridinow in MELLIAND TEXTILBERICHTE 59 [1979]), it will be apparent that the manual separation of the fiber strips is very time-consuming and hardly reproducible. Manual operation demands high skill and moreover entails steady contact between the crude material and the bare skin, whereby sweat contamination cannot be avoided.

SUMMARY OF THE INVENTION

An object of the invention is to provide a universally applicable separation apparatus for fiber webs wound on a processing drum and with parallelized fibers from matted fiber aggregates, this apparatus operating fully automatically and without damaging the fibers.

Briefly described, the invention comprises a separation apparatus for separating a fiber web (6) wound on a processing drum and with parallelized fiber positions comprising the combination of a rocker arm (1) having a separation comb (13). A separation cam has a cam control surface and the rocker arm is mounted for displacement along the control surface of the separation cam (3) to control the movement of the arm and the comb thereby to control the separation of the fiber web (6) from the processing drum (4) at a specific site on the drum and the unwinding of the separated fiber web from the processing drum (4) by means of the free end of the fiber web (6) along a generatrix of the surface of the processing drum (4).

Essentially the advantages offered by the invention are that fiber strips with pre-parallelized fibers are separated from a site at the surface of a processing drum, fully automatically, so that they can then be unwound from the pertinent processing drums.

The separation apparatus of the invention selectively may be linked to a single or to several processing drums. An example of an application using two lined processing drums is described in Swiss patent application 1468/89. Instead of a garnett wire, the fiber-web processing drums also can be equipped with a vacuum device or an electrostatic holding means in order to temporarily retain the fiber web to be processed on the processing drum.

BRIEF DESCRIPTION OF THE DRAWINGS

An illustrative embodiment of the invention is shown in the drawings and will be elucidated below.

FIG. 1 is a schematic side elevation of an apparatus in accordance with the invention cooperating with a single processing drum;

FIG. 2 is a front view, perpendicular to FIG. 1, of the retaining agent, or depressor, and of the garnett wire of the apparatus of the invention;

FIG. 3 is a schematic side elevation of an apparatus in accordance with the invention with additional insertion means for the separated fiber web.

DESCRIPTION OF THE PREFERRED EMBODIMENT

Figure 4:
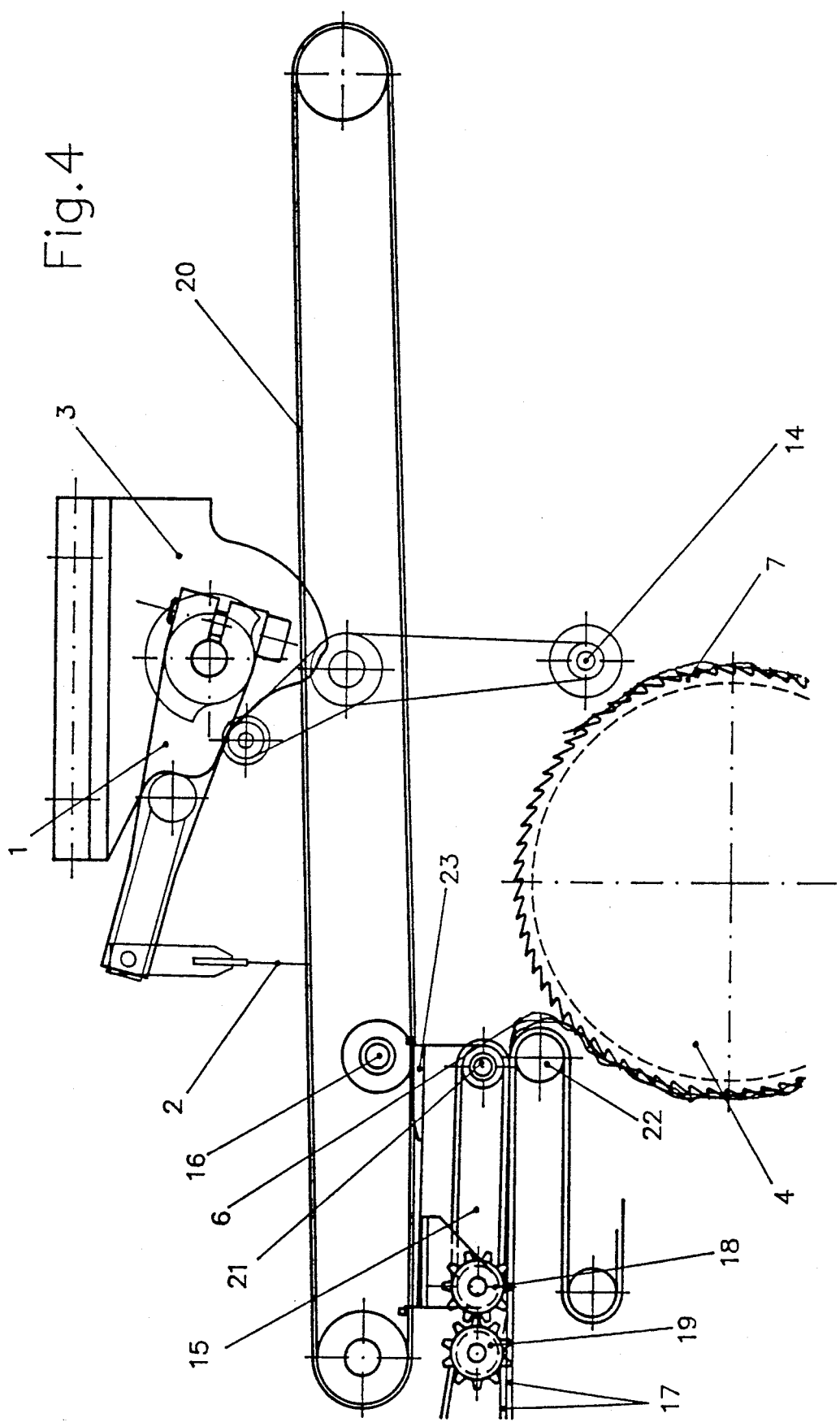
FIG. 4 is a schematic side elevation of an apparatus in accordance with FIG. 3 with drawn-out insertion means.

FIG. 1 shows a preferred embodiment of a separation apparatus in accordance with the invention cooperating with a cylindrical processing drum 4 driven (by conventional means not shown) selectively in either direction of rotation as shown by the arrows A and B and fitted with a garnett wire 7 mounted on the cylinder surface. The specific garnett wire 7 which is shown in the drawing has a sawtooth profile, though it alternatively may have a plurality of small hooks or needles.

The matted, premetered fiber material is fed (by conventional means not shown) to the processing drum 4.

A rocker arm 1, shown in FIG. 1 in three different operative positions, is moved to-and-fro relative to the processing drum 4 and includes four bars or links 9, 10, 11, 12 pivotally connected to each other in the form of a parallelogram and comprises a plurality of needles 2 forming a separation comb 13 attached to one end of bar 10. The lever apparatus including the four bars 9, 10, 11, 12 is mounted so as to be displaceable along the surface of a separation cam 3. The shape of the control surface of separation cam 3 must be determined empirically and most of all depends on the parameters of all the remaining apparatus (for instance the size of the processing drum 4, the length of the arm 1, the kind of fiber web 6, the position and size of the processing stations following the separation apparatus and the variable positions, described below, of the needles 2 of the separation comb 13). The shape of this cam must be selected in such manner that the separation of the fiber web 6 wound on the processing drum 4 takes place at a defined location on the drum and the unwinding of the separated fiber web 6 from the processing drum 4 is carried out by the free end 8 of the fiber web 6 along a generatrix of the surface of processing drum 4.

The motion of the arm 1 and of its coordinates with the position of the pre- or after-positioned processing stations takes place automatically through a control device (not shown).

Position (a) in FIG. 1 shows the arm in its inactive or rest position. Next the arm 1 moves counterclockwise along the separation cam 3 toward the processing drum 4, the lever means so changing the angular position of the needles 2 of the separation comb 13 that the needles 2 are incident tangentially to the drum surface and are inserted into the garnett wire 7 and thereby pierce the fiber web 6 placed thereupon and lift it off of the processing drum 4. As a result, the fiber web 6 is interrupted between the retaining agent, or depressor 5, designed as a roller, and the needles 2 (position b). The separation cam 3 and the lever apparatus 9, 10, 11, 12 with separation comb 13—which in the preferred embodiment is a four-bar parallelogram linkage—then pivots the separation comb 2 in such a way that the tip of the fiber web 8 slips off of the needles 2 (position c).

During separation, the drag-end of the web (i.e., the end of the web from which the specimen is pulled away) is pressed by the depressor 5, which has moved from the rest position 14 into the operational position 14', against the processing drum 4. At its free end, the depressor 5 comprises a roller with a soft coating such as rubber. In a preferred embodiment (FIG. 2), the roller of depressor 5 is fluted, the roller recesses matching the garnett wires 7 of the processing drum 4.

The tip 8 of the fiber web that was separated from the periphery of the processing drum 4 now can be fed to an arbitrary processing station (for instance a drawing means). Purposefully tip 8 of the separated fiber web 6 is inserted, as shown in FIG. 3, into insertion means 15-24. The difficulty with this procedure lies in the fact that the fibers of tip 8 which, at the end of the separating process, are located in a separation comb 2, may not be folded back during the insertion process into the insertion means 15-24, i.e., no hooks should be formed.

This problem can be solved by insertion means 15-24, as shown in detail in FIGS. 3 and 4, which consist mainly of an insertion sled 15 hanging from an upper belt conveyor 20. Insertion sled 15 includes a center belt conveyor 24 which is driven by the toothed wheel 18. In the neutral position the insertion sled 15 is positioned at the right stop of the upper belt conveyor 20. When the separated fiber wib 6 is hanging in the separation comb 2, the insertion sled 15 is advanced thereto by means of the upper belt conveyor 20. Thereupon, processing drum 4 is moved counter-clockwise until fiber web 6 is gliding out of the separation comb 2 and takes its rest on the center belt conveyor 24 of the insertion sled 15 as shown in FIG. 3. Then insertion sled 15, as shown in FIG. 4, is moved to the left stop of the upper belt conveyor 20 where toothed wheels 18 and 19 are meshing. During this process step, fiber web 6 is laid on the lower belt conveyor 17 without folding back the fibers of tip 8 of the separated fiber web 6.

Then the lower belt conveyor 17 and processing drum 4 can be moved in order to draw the separated fiber web 6 off of processing drum 4. Thereby center belt conveyor 24 of insertion sled 15 is simultaneously moved. By means of bridge 23, shaft 16 presses belt conveyor axis 21 against belt conveyor axis 22, causing a clamping site for fiber web 6, aiding the drawing-off of fiber web 6 from processing drum 4.

In the event of repeated processing procedures (for instance parallelizing and stretching the fibers), the separation apparatus of the invention can repeatedly separate the processed fiber web 6 from the same processing drum 4. It is also possible to service a number of processing drums 4 from a single separation apparatus of the invention, whereby such apparatus can be built more simply and more economically.

The separation apparatus of the invention advantageously may be used in equipment for making fiber strips with parallelized fiber positions from matted fiber aggregates such as is described in the Swiss patent application 1468/89.

What is claimed is:

1. A separation apparatus for separating a fiber web (6) wound on a rotatable processing drum having a plurality of rows of garnett elements extending from the surface thereof along circumferential circles lying in planes perpendicular to the rotation axis of the drum, the rows of elements being axially spaced apart, the web having a free end and parallelized fiber positions, the apparatus comprising the combination of
   a rocker arm (1) carrying a separation comb (13);
   a separation cam (3) having a cam control surface;
   means for mounting said rocker arm for movement along said control surface of said separation cam (3) to control the movement of said arm and said comb toward and away from said surface of said drum thereby to engage the free end of the fiber web (6) at a specific site on said drum surface between said rows of garnett elements and to separate and unwind the separated fiber web from the processing drum (4) along a generatrix of the processing drum (4).

2. A separation apparatus according to claim 1, wherein said arm (1) comprises a lever apparatus having a plurality of mutually articulated links, said separation comb (13) being attached to one of said links.

3. A separation apparatus according to claim 2 wherein said lever apparatus includes four links pivotally interconnected in a parallelogram-like arrangement.

4. A separation apparatus according to claim 2 wherein said arm (1) is formed and said control surface is shaped such that said separation comb (13) continuously moves through various angles with respect to said surface of said drum as said arm moves along said separation cam surface (3) and said comb tangentially sweeps said surface of said processing drum (4).

5. A separation apparatus according to claim 4 and further comprising a motor controlling said angular position of said arm (1) along said separation cam (3).

6. A separation apparatus according to claim 5 and further comprising retention means (5) for holding the end of said fiber web (6) opposite said free end against the processing drum (4) during separation.

7. A separation apparatus according to claim 1 and further comprising insertion means (15-24) for engaging the fibers of the separated fiber web (6) and removing the fibers from said separation comb (13) after the free end has been separated from said drum and for drawing the entire web from said processing drum (4)

8. A separation apparatus according to claim 7 wherein said insertion means (15-24) comprises an insertion sled (15) movably by an upper belt conveyor (20).

9. A separation apparatus according to claim 8 wherein said insertion sled (15) comprises a center belt conveyor (24) drivable by a toothed wheel (18).

10. A separation apparatus according to claim 9 wherein said insertion sled (15) is movable between a first end stop of said upper belt conveyor (20) at which said separated fiber web is inserted and a second end stop of said upper belt conveyor (20) at which the separated fiber web (6) is inserted between two belt conveyors.

* * * * *